United States Patent
Bare et al.

(10) Patent No.: US 9,333,333 B2
(45) Date of Patent: *May 10, 2016

(54) OFFSET ELECTRODE

(75) Inventors: Rex O. Bare, Lake Forest, CA (US);
Bradley Sargent, Mission Viejo, CA (US)

(73) Assignee: ETHICON, INC., Somerville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/402,081

(22) Filed: Feb. 22, 2012

(65) Prior Publication Data

US 2012/0145440 A1 Jun. 14, 2012

Related U.S. Application Data

(63) Continuation of application No. 12/605,409, filed on Oct. 26, 2009, now Pat. No. 8,126,530.

(51) Int. Cl.
*A61N 1/00* (2006.01)
*A61N 1/04* (2006.01)
*A61B 5/0408* (2006.01)
*A61N 1/36* (2006.01)

(52) U.S. Cl.
CPC .......... *A61N 1/0456* (2013.01); *A61B 5/04087* (2013.01); *A61N 1/0492* (2013.01); *A61N 1/0496* (2013.01); *A61B 2562/125* (2013.01); *A61N 1/36021* (2013.01)

(58) Field of Classification Search
USPC .......... 174/250–268; 600/392, 394–395, 372, 600/397; 607/72, 142, 152, 153, 149
See application file for complete search history.

(56) References Cited

U.S. PATENT DOCUMENTS

| | | | |
|---|---|---|---|
| 3,977,392 A | 8/1976 | Manley | |
| 4,079,731 A | 3/1978 | Danby | |
| 4,406,288 A | 9/1983 | Horwinski | |
| 4,537,195 A | 8/1985 | McDonnell | |
| 4,617,935 A * | 10/1986 | Cartmell et al. | 600/392 |

(Continued)

FOREIGN PATENT DOCUMENTS

| | | |
|---|---|---|
| EP | 0 504 715 | 9/1992 |
| JP | 6-48690 B2 | 6/1994 |

(Continued)

OTHER PUBLICATIONS

International Search Report in parent counterpart PCT Application No. PCT/US2010/052639, mailed on Jan. 26, 2011 (5 pages).

(Continued)

*Primary Examiner* — Zachary M Pape
(74) *Attorney, Agent, or Firm* — Cohen & Hildebrand, PLLC

(57) ABSTRACT

An electrode including a non-conductive substrate having a top surface and at least one channel extending therethrough, an electrically conductive trace material positioned adjacent a portion of the top surface of the non-conductive substrate and extending through the channel, and adapted for electrically coupling to a power source, and a second electrically conductive material that is inert or more corrosion resistant than the trace material. The second material is positioned adjacent to and entirely covering a top surface of the trace material. The electrode further includes a conductive hydrogel laterally offset from the trace material, the hydrogel may be positioned adjacent to a portion of a top surface of the second electrically conductive material.

8 Claims, 2 Drawing Sheets

(56) References Cited

U.S. PATENT DOCUMENTS

| | | | |
|---|---|---|---|
| 4,719,922 A | 1/1988 | Padjen | |
| 4,777,954 A | 10/1988 | Keusch et al. | |
| 4,979,517 A | 12/1990 | Grossman et al. | |
| 4,981,806 A | 1/1991 | Maas et al. | |
| 4,989,605 A | 2/1991 | Rossen | |
| 5,337,748 A | 8/1994 | McAdams et al. | |
| 5,402,780 A * | 4/1995 | Faasse, Jr. | 600/392 |
| 5,423,874 A | 6/1995 | D'Alerta | |
| 5,562,717 A | 10/1996 | Tippey | |
| 5,702,428 A | 12/1997 | Tippey | |
| 5,824,033 A | 10/1998 | Ferrari | |
| 6,019,877 A | 2/2000 | Dupelle et al. | |
| 6,465,084 B1 * | 10/2002 | Curcio et al. | 428/209 |
| 8,126,530 B2 * | 2/2012 | Bare et al. | 600/397 |
| 8,260,439 B2 | 9/2012 | DiUbaldi et al. | |
| 2001/0050183 A1 * | 12/2001 | Lubert et al. | 174/265 |
| 2003/0233137 A1 | 12/2003 | Paul | |
| 2004/0162602 A1 | 8/2004 | Cohen | |
| 2005/0001324 A1 * | 1/2005 | Dunn et al. | 257/762 |
| 2005/0057906 A1 * | 3/2005 | Nakatani et al. | 361/771 |
| 2005/0277998 A1 | 12/2005 | Tracey | |
| 2006/0025665 A1 | 2/2006 | Dupelle et al. | |
| 2006/0195153 A1 | 8/2006 | DiUbaldi | |
| 2006/0205204 A1 * | 9/2006 | Beck | 438/628 |
| 2008/0132772 A1 | 6/2008 | Lang et al. | |
| 2008/0171929 A1 * | 7/2008 | Katims | 600/391 |
| 2008/0251289 A1 * | 10/2008 | Palmeri et al. | 174/263 |
| 2009/0043185 A1 | 2/2009 | McAdams | |

FOREIGN PATENT DOCUMENTS

| | | |
|---|---|---|
| WO | WO 0197911 | 12/2001 |
| WO | WO 2006113801 | 10/2006 |

OTHER PUBLICATIONS

Copending, co-owned U.S. Appl. No. 12/605,409, filed Oct. 26, 2009.

Japanese Office Action for counterpart Japanese Patent Application No. 2012-536859, mailed Jul. 15, 2014 (3 pages).

* cited by examiner

OFFSET ELECTRODE

CROSS-REFERENCE TO RELATED APPLICATIONS

This application is a continuation application of U.S. patent application Ser. No. 12/605,409, filed Oct. 26, 2009, which is herein incorporated by reference in its entirety.

BACKGROUND OF THE INVENTION

1. Field of the Invention

The present invention relates generally to the construction of electrodes, and more particularly to electrodes used to deliver electrical energy to the skin having a design and construction that is particularly suited to resist corrosion.

2. Description of Related Art

For many years electrodes have been used to deliver electrical energy to the skin for various purposes such as for pain management and muscle stimulation. When used for transdermal applications, stimulation electrodes usually require the use of a conductive liquid or gel, often called a "hydrogel", to provide a continuous and efficient conductive path between the current source and the skin. Conductive hydrogels typically contain salt, and as such can be corrosive to common electrode trace materials, which adversely affects the performance of the electrode. Thus, when designing integrated electrodes for transdermal stimulation, in order for such devices to be commercially viable they must have a sufficiently long shelf life, which requires a design that minimizes or eliminates the ability of the hydrogel to migrate and reach the trace elements over time.

One known method for "isolating" a hydrogel from copper traces in an electrode is to cover the copper with an electrically conductive, but more corrosion resistant or inert substance, such as gold. An example of this is illustrated in FIG. 1, where electrode 100 includes a non-conductive substrate 101 (i.e., fiberglass) having an aperture 102 through which a conductive trace material or conductive pad 103 passes and is subsequently electrically coupled to an integrated circuit 120 or the like that provides power to the electrode. The conductive trace material is also applied across a top surface of the non-conductive substrate. A gold or nickel/gold layer 104 is then applied via the well established ENIG (electroless nickel immersion gold) process over the conductive trace element so as to isolate the trace material from the hydrogel 105 as described above. Gold is well known to be a conductive, but inert material, but is also well known to be expensive. Further, although a gold layer theoretically prevents corrosion, in reality variations and/or imperfection in manufacturing processes, particularly in thin film techniques, result in varying degrees of corrosion over time, which presents challenges when designing products for long-term use and/or when long term shelf-life is needed.

Others have been known to incorporate further additional conductive layers between the copper trace material and the hydrogel in an effort to prevent or minimize corrosion. This solution has been used by Alza Corporation of Mountain View, Calif., and an example of such solution is illustrated in FIG. 2. The non-conductive substrate 201 of the electrode 200 includes a conductive copper trace material 203 on its top surface. Deposited on top of the trace material 203 is one or more additional conductive, but inert or more corrosion resistant layers such as an electrically conductive tape 206 and a silver foil 207. When the electrode is placed on the skin of a patient, the hydrogel 105 is placed between the skin and the additional conductive players. Although incorporation of additional layers between the copper and hydrogel does provide added corrosion protection, it also increases the material and assembly costs for the electrode.

Accordingly, what is needed is an improved electrode design that has reduced material and assembly costs, yet provides sufficient corrosion resistance for use as a commercial, transdermal electrode assembly.

SUMMARY OF THE INVENTION

The present invention provides an electrode having a non-conductive substrate having a top surface and at least one channel extending therethrough, an electrically conductive trace material positioned adjacent at least a portion of the top surface of the non-conductive substrate and extending through the channel, and being adapted to be electrically coupled to a power source. The electrode further includes a second electrically conductive material that is inert or more corrosion resistant than the trace material, and that is positioned adjacent to and entirely covering a top surface of the trace material. A hydrogel is laterally offset from the trace material. The hydrogel may be positioned adjacent to a portion of a top surface of the. second electrically conductive material.

The top surface of the non-conductive substrate may include a recessed portion, and the at least one channel may be positioned within the recessed portion. In yet another embodiment, the electrically conductive trace material is positioned entirely within the recessed portion, and the second electrically conductive material may also be positioned entirely within the recessed portion.

In one embodiment, the trace material is made of copper, and in yet another embodiment, the second electrically conductive material is made of gold/nickel. Further, the third electrically conductive material may be made of silver.

In another alternate embodiment, the electrode may include a foam material positioned adjacent to at least a portion of a top surface of the third electrically conductive material so as to substantially surround the hydrogel.

Also provided is an electrode including a non-conductive substrate having a top surface and a bottom surface and at least one channel extending therethrough, where the non-conductive substrate is made of a flexible material. The electrode further includes a copper trace material positioned adjacent at least a portion of the top surface of the non-conductive substrate and extending through the channel, with the trace material being adapted to be electrically coupled to an electrode power source. The electrode further includes a second conductive material made of gold or gold/nickel, and positioned adjacent so as to cover a top surface of the trace material; and a conductive hydrogel being laterally offset from the trace material. The hydrogel may be positioned adjacent to and covering at least a portion of a top surface of the second conductive material.

In one embodiment, the electrode further includes a foam material substantially surrounding the hydrogel yet leaving a top surface of the hydrogel exposed.

In yet another embodiment, the top surface of the non-conductive substrate includes a recessed portion, and the at least one channel is positioned within the recessed portion.

In alternate embodiments, the electrically conductive trace material is positioned entirely within the recessed portion, and the second electrically conductive material may also be positioned entirely within the recessed portion.

These and other features and advantages of the present invention will become apparent from the following more detailed description, when taken in conjunction with the accompanying drawings which illustrate, by way of example, the principles of the invention.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. For example, although the present invention is described in detail in relation to electrodes for transdermal neurostimulation, it is to be understood that such electrodes have various other uses and applications as will be apparent to those skilled in the art.

Figure 3:
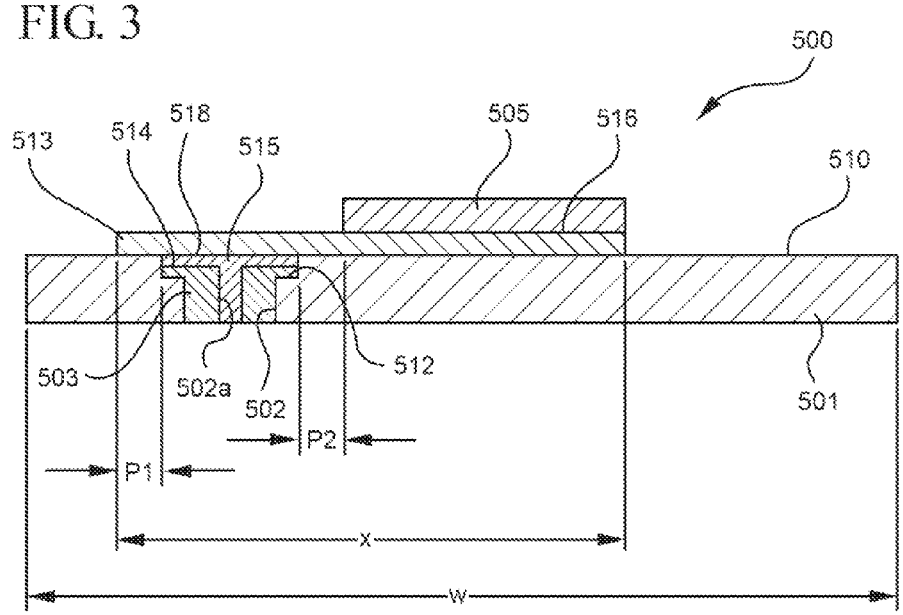
FIG. 3 illustrates one embodiment of an electrode according to the present invention.

FIG. 3 illustrates one exemplary embodiment of an electrode according to the present invention. The electrode 500 includes a non-conductive substrate 501, which may be comprised of any well known material such as FR4 fiberglass or polyamide. The substrate has a lateral width w, a top surface 510 including a recessed portion 512 that surrounds an aperture 502 extending therethrough. Positioned through the aperture 502 and across the recessed portion 512 of the top surface 510 is an electrically conductive trace material 503 such as copper. As used herein, the term "trace material" is intended to mean that which is capable of conducting electricity to form a circuit when electronic components are soldered to it, and may include any type of trace element/material, conductive pads, or the like. The trace material is electrically coupled to a power source (not shown) in a well known manner. This embodiment further includes a second electrically conductive, but inert or more corrosion resistant material 515, preferably gold or gold/nickel, that is applied via a well establish ENIG process so that it both entirely covers the top surface 514 of the trace material 503, but also passes through smaller aperture 502a extending through the trace material as shown. Positioned adjacent to at least a portion of the first surface 510 of the non-conductive substrate and also adjacent to the top surface 518 of the second electrically conductive material 515, and otherwise covering the first electrically conductive material, is a third layer of electrically conductive, but inert or more corrosion resistant material 513. Material 513 covers a width x such that it extends beyond the top surface of the trace material 503 on all respective sides as exemplified by p1 and p2 on FIG. 3. In a preferred embodiment, the third conductive material 513 is silver ink that can be directly applied by known screen-printing techniques.

The hydrogel 505 is applied across a portion of the top surface 516 of third electrically conductive material 513. As illustrated in the embodiment of FIG. 3, the trace material 503 and the hydrogel 505 are laterally offset from one another by distance p2. By "laterally offset" what is meant is that no portion of the hydrogel is positioned directly above any portion of the trace material. In this manner, should there be any imperfections during application of material 513 and 515, the hydrogel is less likely to reach the trace material thru migration than it would if positioned directly over the trace material.

Figure 4:
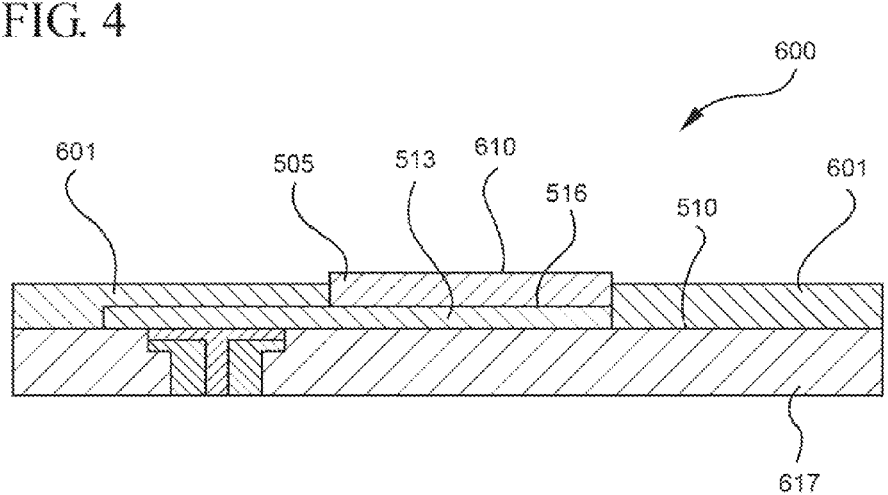
FIG. 4 illustrates yet another embodiment of an electrode according to the present invention.

Finally, a preferred embodiment of the present invention is illustrated in FIG. 4, which is similar to the embodiment of FIG. 3, but incorporates additional features. The electrode 600 of FIG. 4 also illustrates an additional layer of a foam 601 or the like, such as polyurethane, that is laminated directly onto both the exposed top surface 510 of the non-conductive substrate, and also to the top surface 516 of the silver layer 513 to thereby substantially surround the hydrogel 505 while leaving a top surface 610 of the hydrogel exposed. In this manner, the laterally offset hydrogel is prevented from migrating laterally, further reducing the chance of the hydrogel contacting the trace element.

Figure 1:
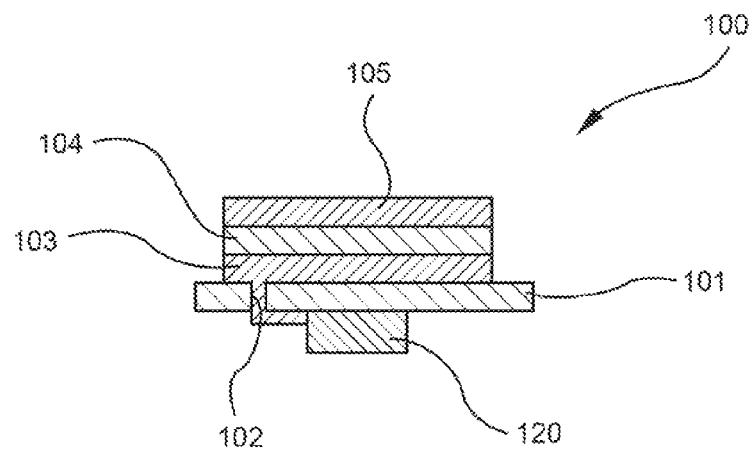
FIGS. 1 and 2 illustrate known prior art electrode assemblies.
Figure 2:
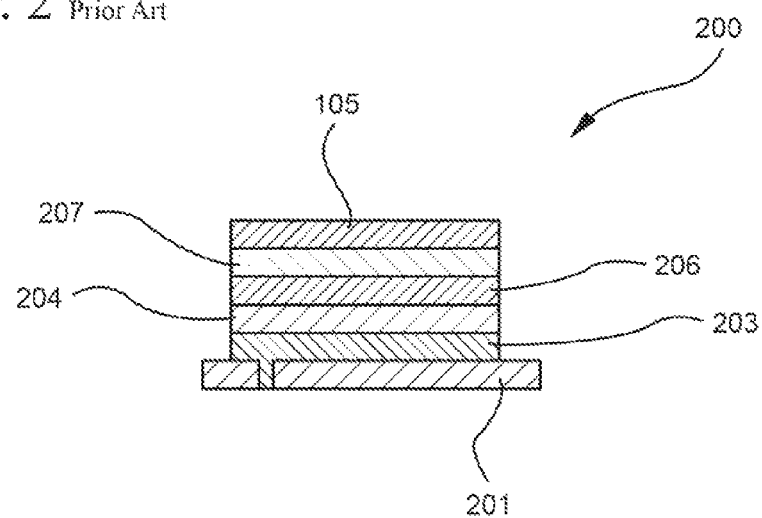

Short term stability tests were carried out on electrodes constructed as shown in FIG. 1 as well as electrodes constructed as shown in FIG. 4. With regard to those constructed as shown in FIG. 1, these electrodes were found to be functional, but with an "unstable" design highly subject to corrosion as a result of manufacturing variability in the deposition of inert material intended to keep the hydrogel and underlying copper separated. Twenty electrodes enclosed in heat sealed foil pouches were tested in an accelerated aging environment chamber at 50 degrees Celsius. Within 3 days all electrodes exhibited green discoloration indicative of corrosion. When the same stability tests were performed on twenty electrodes constructed as shown in FIG. 4, no corrosion was visible after 34 days. The results of these stability tests demonstrate significant improvement in the electrodes of the present invention.

In one preferred embodiment, the electrodes described herein may be incorporated within a transdermal neurostimulation patch of the type illustrated and described in U.S. patent application Ser. No. 11/941,508, filed on Nov. 16, 2007, which is hereby incorporated by reference in its entirety.

While the foregoing describes specific embodiments of the present invention, other and further embodiments may be devised without departing from the basic scope thereof. As such, the scope of the present invention is to be limited only as set forth in the appended claims.

What is claimed is:

1. An electrode comprising:
   a non-conductive substrate having a top surface and a channel extending therethrough; the top surface of the non-conductive substrate having a recessed portion defined therein;
   an electrically conductive trace material positioned adjacent at least a portion of the top surface of the non-conductive substrate entirely within said recessed portion and said channel; and the electrically conductive trace material extending through said channel, and being adapted to be electrically coupled to a power source; and
   a second electrically conductive material that is inert or more corrosion resistant than the trace material, the second electrically conductive material being positioned adjacent to and entirely covering a top surface of the trace material; the second electrically conductive material being positioned entirely within said recessed portion and the channel;
   wherein at least a portion of an outer surface of each of the electrically conductive trace material and the second electrically conductive material is in direct physical contact with the non-conductive substrate.

2. The electrode according to claim 1, wherein the trace material is comprised of copper.

3. The electrode according to claim 1, wherein the second electrically conductive material is comprised of gold or gold/nickel.

4. The electrode according to claim 1, wherein each of the electrically conductive trace material and the second electrically conductive material extend from said recessed portion through said channel to a bottom surface of the non-conductive substrate.

5. The electrode according to claim 1, wherein the electrically conductive trace material encircles the second electrically conductive material in a portion of said channel extending from said recessed portion to a bottom surface of the non-conductive substrate, the electrically conductive trace material does not extend to the top surface of the non-conductive substrate.

6. An electrode comprising;
a non-conductive substrate having a top surface and a bottom surface and a channel extending therethrough, the non-conductive substrate being comprised of a flexible material; the top surface of the non-conductive substrate having a recessed portion defined therein;
a copper trace material positioned adjacent at least a portion of the top surface of the non-conductive substrate entirely within said recessed portion and the channel; and the electrically conductive trace material extending through said channel, said trace material being adapted to be electrically coupled to an electrode power source; and
a second conductive material comprised of gold or gold/nickel, and positioned adjacent to and covering a top surface of said trace material; and the second electrically conductive material being positioned entirely within said recessed portion and the channel;
wherein at least a portion of an outer surface of each of the electrically conductive trace material and the second electrically conductive material is in direct physical contact with the non-conductive substrate.

7. The electrode according to claim 6, wherein each of the electrically conductive trace material and the second electrically conductive material extend from said recessed portion through said channel to a bottom surface of the non-conductive substrate.

8. The electrode according to claim 6, wherein the electrically conductive trace material, encircles the second electrically conductive material in a portion of said channel extending from said recessed portion to a bottom surface of the non-conductive substrate, the electrically conductive trace material does not extend to the top surface of the non-conductive substrate.

\* \* \* \* \*